United States Patent
Landegren et al.

[11] Patent Number: 6,140,135
[45] Date of Patent: Oct. 31, 2000

[54] MULTIFUNCTIONAL SURFACES

[76] Inventors: Ulf Landegren, Eksoppsvägen 16, S-756 46 Uppsala, Sweden; Alexander Khorlin, 10634 Tuppence Ct., Rockville, Md. 20850; Maritha Mendel-Hartvig, Rabenius väg 28, S-756 55 Uppsala; Ove Öhman, Asplunda, Uppsala-Näs, S-755 91 Uppsala, both of Sweden

[21] Appl. No.: 08/817,564

[22] PCT Filed: Nov. 28, 1995

[86] PCT No.: PCT/SE95/01420

§ 371 Date: Jun. 17, 1997

§ 102(e) Date: Jun. 17, 1997

[87] PCT Pub. No.: WO96/17246

PCT Pub. Date: Jun. 6, 1996

[30] Foreign Application Priority Data

Nov. 30, 1994 [SE] Sweden ........................... 9404166

[51] Int. Cl.[7] .................................... G01N 33/543
[52] U.S. Cl. ..................... 436/518; 422/68.1; 435/287.1
[58] Field of Search ............... 436/518; 435/6, 435/287; 422/68.1, 56

[56] References Cited

U.S. PATENT DOCUMENTS

| | | | |
|---|---|---|---|
| 4,116,638 | 9/1978 | Kenoff | 422/99 |
| 4,225,575 | 9/1980 | Piasio et al. | 424/1 |
| 4,558,013 | 12/1985 | Marinkovich et al. | 436/513 |
| 4,567,149 | 1/1986 | Sell et al. | 436/513 |
| 4,657,869 | 4/1987 | Richards et al. | 435/287 |
| 4,708,931 | 11/1987 | Christian | 435/7 |
| 4,743,541 | 5/1988 | Higgins | 435/7 |
| 4,981,653 | 1/1991 | Marino | 422/56 |
| 5,063,081 | 11/1991 | Cozzette et al. | 427/2 |
| 5,082,768 | 1/1992 | Burd et al. | 435/7.92 |
| 5,215,716 | 6/1993 | Arai | 422/56 |
| 5,324,401 | 6/1994 | Yeung et al. | 204/180.1 |
| 5,405,783 | 4/1995 | Pirrung et al. | 436/518 |
| 5,424,186 | 6/1995 | Fodor et al. | 435/6 |
| 5,445,934 | 8/1995 | Fodor et al. | 435/6 |
| 5,451,683 | 9/1995 | Barrett et al. | 548/302.7 |

(List continued on next page.)

FOREIGN PATENT DOCUMENTS

| | | |
|---|---|---|
| 83 01308 | 4/1982 | WIPO . |
| 87 03965 | 7/1987 | WIPO . |
| WO89/10977 | 11/1989 | WIPO . |
| WO94/11421 | 5/1994 | WIPO . |
| 95 35505 | 12/1995 | WIPO . |

OTHER PUBLICATIONS

"A Novel Method for the Analysis of Multiple Sequence Variants by Hybridisation to Oligonucleotides"—Uwe Maskos and Edwin M. Southern Dept. of Biochemistry, University of Oxford, Nucleic Acids Research, 1993, vol. 21, No. 9, 2267–2268.

"Single–Base Mutational Analysis of Cancer and Genetic Diseases Using Membrane Bound Modified Oligonucleotides"—Yong Zhang, M.Y. Coyne, S.G. Will, C.H. Levenson, E.S. Kawasaki; Dept. of Human Genetics and Nucleic Acid Chemistry, Nucleic Acids Research, vol. 19, No. 14, 3929–3933, 1991.

"Light–Directed, Spatially Addressable Parallel Chemical Synthesis"—Stephen P.A. Fodor, J.L. Read, M.C. Pirrung, L. Stryner, A.T. Lu, D. Solas; Affymax Research Institute; Science, vol, 251; Feb. 15, 1991; 767–773.

*Primary Examiner*—James C. Housel
*Assistant Examiner*—Ginny Allen Portner
*Attorney, Agent, or Firm*—Birch, Stewart, Kolasch & Birch, LLP

[57] ABSTRACT

Array, and methods for the production thereof, of selected immobilized molecules for interaction analysis in which each molecule has a predetermined, identifiable position in the array. The array is obtainable by and the methods are characterized by the following steps: a) bundling and fixing together flat or elongated, thin carrier elements in a regular way, each element having immobilized thereto a selected molecule and having an identifiable position in the array, b) sectioning the bundles and optionally, c) depositing the sections on a support.

8 Claims, 1 Drawing Sheet

U.S. PATENT DOCUMENTS

| | | | |
|---|---|---|---|
| 5,498,324 | 3/1996 | Yeung et al. | 204/452 |
| 5,516,644 | 5/1996 | Yamauchi et al. | 435/7.9 |
| 5,552,272 | 9/1996 | Bogart et al. | 435/6 |
| 5,552,322 | 9/1996 | Nemoto et al. | 435/287.2 |
| 5,556,529 | 9/1996 | Nemoto | 204/612 |
| 5,605,662 | 2/1997 | Heller et al. | 422/68.1 |
| 5,632,957 | 5/1997 | Heller et al. | 422/68.1 |
| 5,648,213 | 7/1997 | Reddy | 435/6 |
| 5,763,263 | 6/1998 | Dehlinger | 435/287 |
| 5,804,384 | 9/1998 | Muller et al. | 435/6 |
| 5,812,272 | 6/1998 | King et al. | 356/445 |
| 5,814,524 | 9/1998 | Walt et al. | 436/518 |
| 5,843,767 | 12/1998 | Beattie | 435/287.1 |

MULTIFUNCTIONAL SURFACES

The present Application is a 371 of PCT/SE95/01420 filed Nov. 28, 1995, the contents of which is hereby incorporated by reference.

The present invention relates to arrays of selected immobilized molecules for interaction analysis and processes for the production thereof. More precisely the invention relates to arrays in which each molecule has a predetermined, identifiable position in the array. The array is obtainable by bundling and fixing together flat or elongated, thin carrier elements, each element having immobilized thereto a selected molecule and finally sectioning the bundles.

Two-dimensional arrays of molecules will become an important type of devices in many analytical approaches. The general benefit of such devices is the potential for rapid, simultaneous analysis with respect to large numbers of entities. It is already known to use arrays of molecules, e.g. biomolecules such as oligonucleotides, peptides etc. in devices for interaction analysis. According to WO 89/10977, an array of the whole or a chosen part of a complete set of oligonucleotides is attached to a surface, which oligonucleotides are capable of taking part in hybridization reactions. In this document as well as in others it is suggested to produce the array by some sort of printing device. An array of the oligonucleotides could be laid down on a surface by using a pen plotter, a laser typesetter or an ink jet printer for example. Another method to construct large arrays of e.g. peptides is suggested which combines solid phase organic chemistry, photo-labile protecting groups and photolitography (Fodor, S. P. A.,Read, J. L., Pirrung, M. C., Stryer, L., Lu, A. T. and Solas D. (1991) Science 251, 76–773). A surface is derivatized with amine linkers which are blocked by photochemically cleavable protecting groups. The surface is selectively irradiated with light to liberate free amines, which can be coupled to photochemically blocked building blocks. The process is repeated with different regions of the synthesis surface being exposed to light, until a desired array of compounds is prepared. The pattern of photolysis and the order of addition of building blocks define the products and their locations. In other methods with solid phase chemistry oligonucleotide arrays were built by directing the base additions to channels created by barrier between plates; alternate bases are added through channels placed at right angles to the previous addition and finer spacing is used as the length of the oligonucleotides and the complexity of the set increases. (Nucleic Acids Research, 1993, Vol. 21, No. 9 2267–2268). These methods are however tedious and time consuming where each array has to be produced individually dot by dot using printing devices or synthesizing each dot individually on site. Another draw back with the generating of the required compound on site is that it is not possible to check the correctness of the obtained molecule before it is immobilized.

The object of the present invention is to provide improved methods for the production of arrays of molecules.

A further object of the present invention is to offer improved arrays of immobilized molecules and especially arrays obtainable by the methods according to the invention.

These objects are achieved by the array and the methods for the production thereof as claimed in the claims. According to the invention a layer of a two dimensional array of interconnected and regularly ordered carrier elements is obtained, each individual element having immobilized thereto a selected molecule and having an identifiable position in the array.

According to one aspect of the invention, there is obtained an array of selected immobilized molecules for interaction analysis in which each molecule has a predetermined, identifiable position in the array. The array is obtainable by
 a) bundling and fixing together flat or elongated, thin carrier elements in a regular way, each element having immobilized thereto a selected molecule and having an identifiable position in the array
 b) sectioning the bundles and optionally
 c) depositing the sections on a support.

According to a further aspect the invention provides a method for the production of an array of selected immobilized molecules for interaction analysis in which each molecule has a predetermined, identifiable position in the array, characterized in the following steps:
 a) bundling and fixing together elongated thin carrier elements in a regular way, each element having immobilized thereto a selected molecule and having an identifiable position in the array
 b) sectioning the bundles and optionally
 c) depositing the sections on a support.

According to a further aspect the invention provides a method for the production of an array of selected immobilized molecules for interaction analysis in which each molecule has a predetermined, identifiable position in the array, characterized in the following steps:
 a) bundling and fixing together flat thin carrier elements in a regular way, each element having immobilized thereto a selected molecule and having an identifiable position in the array
 b) sectioning the bundles and optionally
 c) depositing the sections on a support.

With the present invention a large number of arrays can be made in an inexpensive manner from one single bundle. The sectioning results in "salami-like" slices which can be used as such or can be deposited on a support. There is no need for any type of printing equipment and it is not necessary to immobilize each selected molecule more than once. The required technologies for the production of the arrays, i.e. immobilization, bundling, sectioning, are already known from other contexts. With the present invention with carrier elements there is no risk for contamination between nearby molecules. Further, with the present invention arrays of, for example, oligonucleotides can be synthesized in or on carrier elements. These elements are combined in bundles to generate a two dimensional array. With the present invention it is possible to check that the molecules to be immobilized are the correct, required ones before the array is created. It is also possible to control a section of a carrier element for a successful immobilization.

The array according to the invention comprises regularly ordered and interconnected carrier elements, which have an identifiable position in the array. Each individual element is immobilized with a selected molecule. The carrier elements are flat or elongated thin elements. In one preferred embodiment of the invention the elongated elements are capillaries containing the immobilized molecules. Sets of micro capillaries are filled with particles to which the molecules have been affixed. Each capillary receives a selected molecule and the particles are fixed inside the capillaries in a suitable way e.g. as in WO 94/11421. As an alternative the molecules can be coupled to or synthesized on the internal surface of the capillaries. The capillaries can be made of different material such as glass, plastic e.g. polypropene and polyvinylidenefluoride, polystyrene etc.

In another preferred embodiment the elongated elements are threads to which the molecules have been immobilized, each thread having one selected molecule. The threads can be of cellulose, dextran, plastic etc.

In a further embodiment the elements are formed by passing a mixture of a polymer having a functional group e.g. an allylic or acrylic group and the selected molecules with the same functional groups, through a nozzle. There is one type of selected molecule per hole in the nozzle. The polymer is cross-linked and the molecules thereby immobilized. Another possibility is to chemically bind the selected molecules to the monomers which are then polymerized.

In yet a further embodiment the threads are formed from a polymer and the selected molecules are affixed to the thus formed threads.

Figure 1:
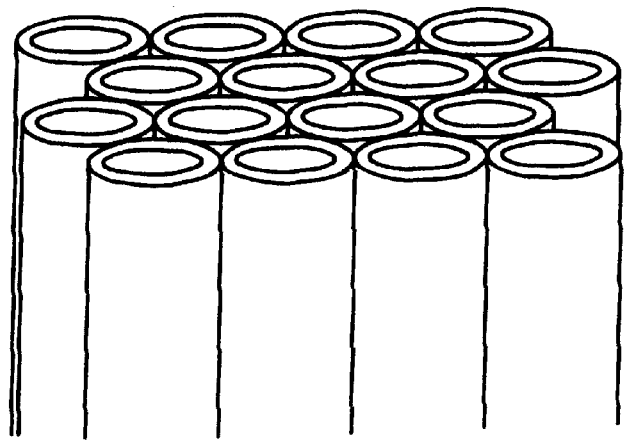
FIG. 1: Elongated elements are bundled in a regular way, permitting precise orientation of the individual elements.

The elongated elements are bundled in a regular way, permitting the precise orientation of the individual elements with respect to one another throughout the length of the bundle (see FIG. 1). A similar technique is used in the manufacture of fibreoptical devices. The bundled capillaries are cast in a material, e.g. an embedding resin, which seals the spaces between them. This material cannot access the interior of the capillaries.

In the case of threads these are suitably placed abreast, after each other, on a sticky surface, layer by layer. They can also be placed in a template with slits, layer by layer. A further possibility is to thread the threads through a guide like a nozzle. The threads are held together with some casting material, for example a resin, or when formed through the nozzle, sticked together when produced. In the case with bundling with a nozzle each hole in the nozzle should have its own identity with a separate container/feed.

The flat carrier elements can be in the form of membranes to which the molecules have been immobilized, one selected molecule to each membrane. They can also be constituted of a carrier surface to which matrices with an immobilized selected molecule have been fixed. The flat elements are bundled together and can be fixed by gluing to a carrier or with double adhering tape. The bundled flat elements can also be coupled to each other by chemical groups or via casting material, such as embedding resin.

Figure 2:
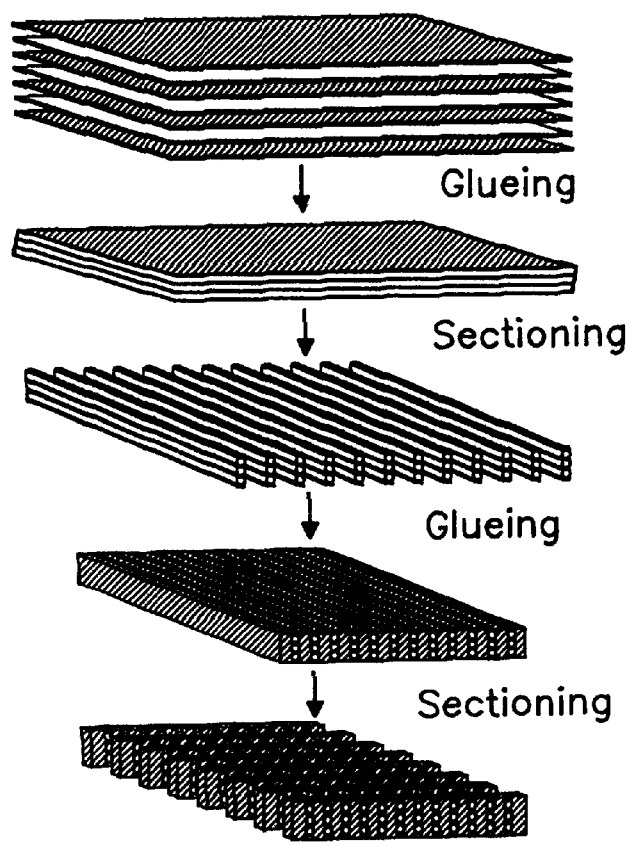
FIG. 2: Sections from several different bundles can be stacked and fixed together and sectioned again.

The bundled elements are then sectioned, for example in a microtome or with laser sectioning, thereby generating a large number of sections with perfectly ordered molecules. Depending on the material of the thin carrier element the sections can be self supporting or the sections can be deposited on a support, suitably a flat surface. In case of sectioned bundles of flat elements, sections from several different bundles can be stacked and fixed together anew and the stacks can be sectioned once again (see FIG. 2). In this way large arrays of many selected molecules can be created.

The orientation of the individual carrier elements is obtained by one or more positioning marks. The positioning can be in the form of a visual mark such as holes or slits or a fluorescent mark. Other possibilities are special positioning strings added to the bundles or a rectangular corner element forming a part of the outer border of the bundle.

The immobilization of the molecules is obtained by conventional methods and is dependent of which kind of molecules the array is to include. For example if an array of oligonucleotides is to be produced, the thread or membrane can be preactivated with carbodiimide, (according to Zang Y. et al, Nucleic Acids Research, Vol. 19, No. 14, 3929–3933) or with N-succinimidyl 3-(2-pyridyldithio) propionate (SPDP) and the oligonucleotide is then covalently coupled through a primary amine or thiol group, respectively, at its end depending on the coupling chemistry. It is also possible to preactivate the thread or membrane with other methods such as with corona discharge treatment or plasma treatment.

If the oligonucleotide is coupled to a polymer or monomer before the thread formation, a monomer with an active group such as an unsaturated carbo-carbo double bond or an alkene group, e.g. an allylic- or acrylic group is mixed with the oligonucleotide with the same group at its end. The coupling is made by radical initiation by UV irradiation. For arrays of other types of molecules the skilled man can easily use coupling methods conventional for the selected molecule.

The array and the methods for the production thereof according to the invention can be applied to a great number of different molecules of which can be mentioned oligonucleotides, DNA, RNA, peptides, proteins, antibodies. The multifunctional surfaces obtained with the array can be used for analysis of interaction between two kinds of molecules such as DNA-DNA, DNA-RNA, DNA-protein, receptor-ligand, antibody-antigen, lectins-glycoproteins, etc.

The arrays can be used in many different applications, for example:

*) Screening of different types of libraries, so called chemical-, phage-, peptide-, oligonucleotide libraries.
 *) when searching for specific motifs in DNA, for example promoters, enhancers.
 *) when searching for homologies between and within a species.
 *) when developing chemical analogues (chemical libraries)
 *) in genetic diagnostic (point mutations, deletions)
 *) in mapping, e.g. of epitopes, DNA (micro satellite, finger printing)
 *) in verifying, for example DNA sequencing
 *) in purification of several components of interest in the same sample
 *) as sample carrier The invention will now be illustrated with the following example which, however, is not intended to limit the invention:

EXAMPLE 1

Membranes of the type Pall Biodyne C, 0,45 $\mu$m, 100 cm$^2$ are activated.

The membranes are washed in 0.1 M HCl, water, ethanol and then acetonitrile. The membranes are dried in a vacuum drier for 2 h.

Activating solution:

2.06 g DCC (N,N'-dicyclohexylcarbodiimide 10 mmol)

1.17 g NHS (N-hydroxy-succinimide 10 mmol) are dissolved in 100 ml dry acetonitrile.

The solution is added to the membranes and these are incubated in motion at ambient temperature over night.

The membranes are washed in dry acetonitrile and then dried in a vacuum drier for 2 h.

Coupling: oligonucleotide synthesized with a —NH$_2$ group in the 5'-end is mixed in a coupling buffer to a concentration of about 10 nmol/ml.

0.6 M Sodium bicarbonate buffer pH 8.5, 1 M NaCl

The coupling buffer containing the oligonucleotide is added to the membranes, which are then incubated in motion for 1 h at ambient temperature.

The membranes are washed 3 times with washing buffer: 10 mM Tris-HCl pH 7.5, 0.1 M NaCl, 0.1% Triton X-100

Bundling: Membranes are mounted on double adhering tape, layer by layer, with tape between the layers.

The bundle is embedded in embedding resin and is sectioned in about 100 μm sections. At the same time as the embedding a positioning mark is added. The sections are mounted on a support.

What is claimed is:

1. A method for the production of an array of selected immobilized molecules for interaction analysis in which each molecule has a predetermined, identifiable position in the array, comprising the following steps:
   a) bundling and fixing together flat thin carrier elements in a regular way, each element having immobilized thereto a selected molecule and having an identifiable position in the array
   b) sectioning the bundled elements
   c) stacking sections from said bundled elements, wherein several different bundles are stacked; and sectioning the stack, and optionally
   d) depositing the sections on a support.

2. The method according to claim 1, wherein that the elements are capillaries containing the immobilized molecules.

3. The method according to claim 1, wherein the elements are threads to which the molecules have been immobilized.

4. The method according to claim 1, wherein the elements are membranes to which the molecules have been immobilized.

5. The method according to claim 1, wherein each element is constituted of a carrier film to which matrices with an immobilized selected molecule has been fixed.

6. The method according to claim 1, wherein the orientation of the individual elements is obtained by one or more positioning marks.

7. The method according to claim 1, wherein the positioning mark is in the form of a visual mark such as a hole or a slit or a fluorescent mark.

8. The method according to claim 1, wherein the molecules are selected from the group consisting of oligonucleotides, DNA, RNA, peptides, proteins, antibodies and lectines.

* * * * *